US011219718B2

(12) United States Patent
Kanazawa et al.

(10) Patent No.: US 11,219,718 B2
(45) Date of Patent: Jan. 11, 2022

(54) SYRINGE

(71) Applicants: TAKEDA PHARMACEUTICAL COMPANY LIMITED, Osaka (JP); ARTE CORPORATION, Tokyo (JP)

(72) Inventors: Atsushi Kanazawa, Takahagi (JP); Kiyotaka Kamata, Takahagi (JP); Akihiko Ono, Osaka (JP); Tomoyuki Manoshiro, Fujisawa (JP); Jiichi Arai, Osaka (JP); Naoki Choda, Nagoya (JP)

(73) Assignees: TAKEDA PHARMACEUTICAL COMPANY LIMITED, Osaka (JP); ARTE CORPORATION, Tokyo (JP)

( * ) Notice: Subject to any disclaimer, the term of this patent is extended or adjusted under 35 U.S.C. 154(b) by 176 days.

(21) Appl. No.: 16/497,492

(22) PCT Filed: Mar. 13, 2018

(86) PCT No.: PCT/JP2018/009691
§ 371 (c)(1),
(2) Date: Sep. 25, 2019

(87) PCT Pub. No.: WO2018/180458
PCT Pub. Date: Oct. 4, 2018

(65) Prior Publication Data
US 2021/0106760 A1 Apr. 15, 2021

(30) Foreign Application Priority Data
Mar. 31, 2017 (JP) .............................. JP2017-071731

(51) Int. Cl.
*A61M 5/31* (2006.01)
*A61M 5/315* (2006.01)

(52) U.S. Cl.
CPC ...... *A61M 5/3137* (2013.01); *A61M 5/31511* (2013.01); *A61M 2005/3139* (2013.01)

(58) Field of Classification Search
CPC ............ A61M 5/3137; A61M 5/31511; A61M 2005/3139; A61M 5/3129; A61M 5/31
See application file for complete search history.

(56) References Cited

U.S. PATENT DOCUMENTS

| 2009/0182284 A1* | 7/2009 | Morgan | .............. | A61M 5/3202 |
| | | | | 604/198 |
| 2014/0005610 A1* | 1/2014 | Kakiuchi | .......... | A61M 5/31586 |
| | | | | 604/224 |

FOREIGN PATENT DOCUMENTS

| CN | 101945679 A | 1/2011 |
| CN | 103228308 A | 7/2013 |

(Continued)

OTHER PUBLICATIONS

Rule 70 Communication dated Aug. 6, 2020 corresponding to European application No. 18777385.8-1122.

(Continued)

*Primary Examiner* — Brandy S Lee
*Assistant Examiner* — Hong-Van N Trinh
(74) *Attorney, Agent, or Firm* — Nath, Goldberg & Meyer; Joshua B. Goldberg

(57) ABSTRACT

The present invention improves the feeling in use when a finger is hooked on a finger grip. This syringe is provided with a cylinder 22, a syringe needle 24, a finger grip 30, and a plunger rod 32. The finger grip 30 is provided with a cylindrical portion and a pair of finger hook portions. The finger hook portion has an inclined curved surface 70 and an end-side curved surface 72. The inclined curved surface 70 is disposed on a side, of a side surface of the finger hook portion, connected to the cylinder 22. In the inclined curved surface 70, the inclination of a base-side region with respect to the center axis of the cylindrical portion is gentler than the inclination of an end-side region with respect to the center axis of the cylindrical portion. The end-side curved surface (Continued)

72 is disposed at the boundary between the end of the finger hook portion and the inclined curved surface 70. The end-side curved surface 72 extends along the boundary.

5 Claims, 13 Drawing Sheets

(56) References Cited

FOREIGN PATENT DOCUMENTS

| WO | 2004/073774 A1 | 9/2004 |
| WO | 2013159059 A1 | 10/2013 |
| WO | 2013178771 A1 | 12/2013 |
| WO | 2014184321 A1 | 11/2014 |

OTHER PUBLICATIONS

European Search Report dated Jul. 20, 2020 corresponding to application No. 18777385.8-1122.
First Office Action dated Apr. 30, 2021, for corresponding Chinese application 201880023012.2.

* cited by examiner

FIG. 11

| | Working Example 1 | Working Example 2 | Working Example 3 | Working Example 4 | Working Example 5 | Working Example 6 |
|---|---|---|---|---|---|---|
| Drawing | 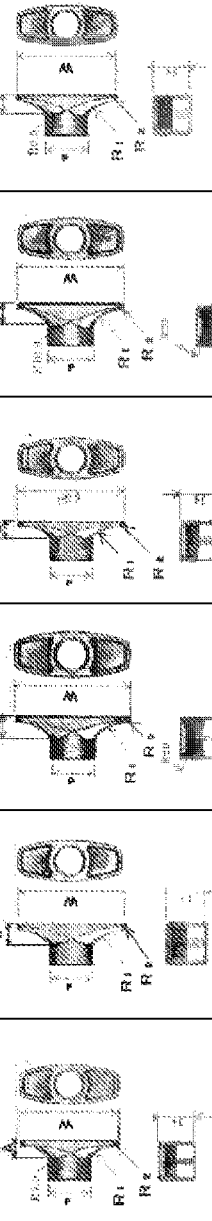 | 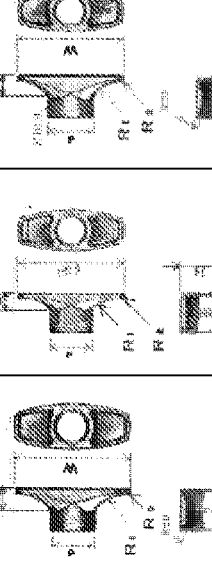 | 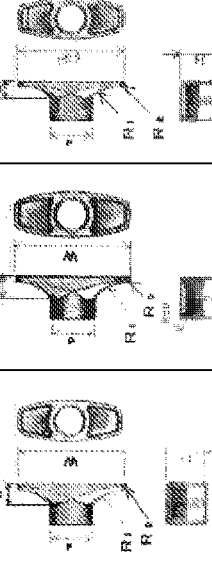 | 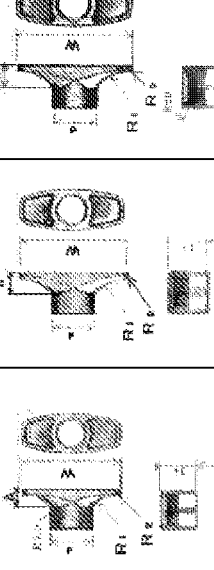 | 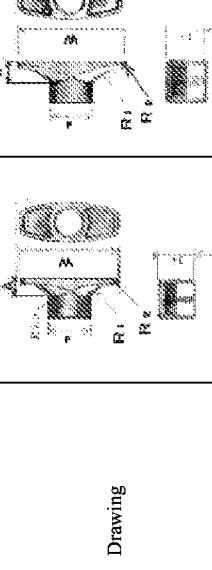 |  |
| Entire width of finger hook portion W [mm] | 38 | 35 | 38 | 38 | 35 | 35 |
| Radius of curvature of inclined curved surface $R_1$ [mm] | 15.8 | 10 | 15.8 | 10 | 12.5 | 12.5 |
| Radius of curvature of end-side curved surface $R_2$ [mm] | 1.5 | 0.4 | 0.4 | 0.4 | 0.4 | 1.5 |
| Outside diameter of cylindrical portion d [mm] | 15 | 15 | 15 | 15 | 15 | 15 |
| Entire width of finger hook portion -2 × Radius of curvature of end-side curved surface - Outside diameter of cylindrical portion [mm] | 20 | 19.2 | 22.2 | 22.2 | 19.2 | 17 |
| Height of finger hook portion A [mm] | 7.1 | 6.3 | 7.1 | 6.3 | 7.1 | 7.1 |
| Number of votes — 1st & 2nd | 5 | 4.67 | 3.67 | 3.33 | 2 | 1.33 |
| Number of votes — 1st only | 3 | 1.33 | 2 | 3 | 1.67 | 0.33 |

FIG. 12

| | Operation steps | | Syringe ranked first in score average | Score | |
|---|---|---|---|---|---|
| | | | | Average | Deviation |
| Drug preparation | First step | Ease of dispersing medium/fluid motion (ease with which rod is pressed) | Working Example 1 | 0.56 | 0.62 |
| | Second step | Ease of microcapsule suspension | Working Example 1 | 0.44 | 0.50 |
| | Third step | Ease of air removal (ease with which rod is pressed) | Comparative Example 1 | 0.41 | 0.56 |
| | Fourth step | Ease of needle insertion | Working Example 1 | 0.28 | 0.52 |
| Subcutaneous injection | Fifth step | Ease of blood backflow check (ease with which rod is pulled) | Working Example 2 | 0.50 | 0.62 |
| | Sixth step | Ease of complete discharge of liquid content (ease with which rod is pressed) | Working Example 1 | 0.47 | 0.57 |

FIG. 13

| Operation steps | | | Working Example / Comparative Example | Answer [%] | | | Score average rank |
|---|---|---|---|---|---|---|---|
| | | | | Worse | Same | Better | |
| Drug preparation | First step | Ease of dispersing medium/fluid motion (ease with which rod is pressed) | Working Example 1 | 6.3 | 31.3 | 62.5 | 1 |
| | | | Working Example 2 | 25.0 | 40.6 | 34.4 | 3 |
| | | | Comparative Example 1 | 18.8 | 50.0 | 31.3 | 2 |
| | Second step | Ease of microcapsule suspension | Working Example 1 | 0.0 | 56.3 | 43.8 | 1 |
| | | | Working Example 2 | 12.5 | 50.0 | 37.5 | 2 |
| | | | Comparative Example 1 | 3.1 | 68.8 | 28.1 | 2 |
| | Third step | Ease of air removal (ease with which rod is pressed) | Working Example 1 | 3.1 | 56.3 | 40.6 | 2 |
| | | | Working Example 2 | 18.8 | 46.9 | 34.4 | 3 |
| | | | Comparative Example 1 | 3.1 | 53.1 | 43.8 | 1 |
| Subcutaneous injection | Fourth step | Ease of needle insertion | Working Example 1 | 3.1 | 65.6 | 31.3 | 1 |
| | | | Working Example 2 | 12.5 | 78.1 | 9.4 | 3 |
| | | | Comparative Example 1 | 0.0 | 90.6 | 9.4 | 2 |
| | Fifth step | Ease of blood backflow check (ease with which rod is pulled) | Working Example 1 | 12.5 | 31.3 | 56.3 | 2 |
| | | | Working Example 2 | 6.3 | 37.5 | 56.3 | 1 |
| | | | Comparative Example 1 | 0.0 | 59.4 | 40.6 | 3 |
| | Sixth step | Ease of complete discharge of liquid content (ease with which rod is pressed) | Working Example 1 | 3.1 | 46.9 | 50.0 | 1 |
| | | | Working Example 2 | 12.5 | 50.0 | 37.5 | 2 |
| | | | Comparative Example 1 | 6.3 | 71.9 | 21.9 | 3 |

SYRINGE

This is a National Phase Application filed under 35 U.S.C. 371 as a national stage of PCT/JP2018/009691, filed Mar. 13, 2018, an application claiming the benefit of Japanese Application No. 2017-071731, filed Mar. 31, 2017, the content of each of which is hereby incorporated by reference in its entirety.

TECHNICAL FIELD

The present invention relates to a syringe.

BACKGROUND ART

Patent Document 1 discloses a syringe. This syringe includes a cylinder having a needle mount and a bypass structure, a finger grip, and a plunger rod. The needle mount is attached to the distal end of the cylinder. A plug accommodating chamber is formed inside the needle mount. A communication groove in the form of a recess is formed in an inner wall of this plug accommodating chamber. A syringe needle is attached to the needle mount at the opposite end from the side connected to the cylinder. At the distal end inside the cylinder is mounted a front plug, and successively from there a middle plug and an end plug. The finger grip is attached at the rear end of the cylinder such as to surround part of the circumference of the cylinder. Further, the plunger rod is attached to the rear end of the cylinder.

PRIOR ART DOCUMENTS

Patent Documents

Patent Document 1: WO 2004/073774

SUMMARY OF THE INVENTION

Problems to be Solved by the Invention

The syringe disclosed in Patent Document 1 has a problem that the sense of feel when in use with fingers rested on the finger grip is not favorable. The interior of the syringe of Patent Document 1 is divided to a first chamber and a second chamber by the bypass structure and the stoppers. When the plunger rod of this syringe is pushed forward, the stoppers of the syringe move, so that the first chamber and the second chamber connect to each other via the bypass. As the plunger rod is further pushed forward, the inner space of the cylinder connects to the syringe needle via the communication groove of the needle mount. Not just the syringe of Patent Document 1, but in general, when the plunger rod of the syringe is pushed forward, fingers are rested on the finger grip to stabilize the syringe. The finger grip not having a favorable feel when in use means that the finger grip causes a pain in the finger, the finger grip lacks stability, or the finger grip hardly allows smooth transmission of force to the plunger rod, when the plunger rod is pushed forward with fingers rested on the finger grip. For medical workers, the finger grip not having a favorable feel when in use may cause an increased sense of tiredness in repeated administration, or an increase in time required for preparation of drugs.

The present invention was made to solve these problems. An object of the present invention is to provide a syringe with an improved sense of feel when in use with fingers rested on the finger grip.

Solutions to the Problems

Through intensive investigation of the problems described above, the inventors found out that the shape of finger hook portions of the finger grip has a large impact on the sense of feel when in use with fingers rested thereon, which led to the completion of the present invention. Namely, the present invention is as follows:

The first aspect of the invention is a syringe including:
a cylinder;
a syringe needle connected to one end of the cylinder;
a finger grip connected to the other end of the cylinder; and
a plunger rod passing through the finger grip and entering into the cylinder,
the finger grip including
a cylindrical portion having one end and the other end, the cylinder being inserted from the one end, and the plunger rod extending through from the other end of the cylindrical portion, and
a pair of finger hook portions protruding from an outer circumferential surface of the cylindrical portion to opposite directions,
the finger hook portion including
an inclined curved surface located on one side surface of the finger hook portion facing the one end of the cylindrical portion and having an area on a proximal side of the side surface and an area on a distal side of the side surface, the area on the distal side of the side surface being closer to the other end of the cylindrical portion than the area on the proximal side of the side surface, and the area on the proximal side having a shallower slope with respect to a center axis of the cylindrical portion than the area on the distal side, and
an end-side curved surface disposed in a boundary between a tip of the finger hook portion and the inclined curved surface and extending along the boundary.

The second aspect of the invention is characterized in that, in addition to the configuration according to the first aspect of the invention,
the end-side curved surface extends as far as to the tip of the finger hook portion, and
a length obtained by subtracting twice a radius of curvature of the end-side curved surface and an outside diameter of the cylindrical portion from a length between the tip of one finger hook portion and the tip of the other finger hook portion is 19.2 mm or more.

The third aspect of the invention is characterized in that, in addition to the configuration according to the second aspect of the invention,
the length obtained by subtracting twice a radius of curvature of the end-side curved surface and an outside diameter of the cylindrical portion from a length between the tip of one finger hook portion and the tip of the other finger hook portion is 22.2 mm or less.

The fourth aspect of the invention is characterized in that, in addition to the configuration according to the second aspect of the invention,
the length obtained by subtracting twice a radius of curvature of the end-side curved surface and an outside diameter of the cylindrical portion from a length between the tip of one finger hook portion and the tip of the other finger hook portion is 20 mm or less.

The fifth aspect of the invention is characterized in that, in addition to the configuration according to the fourth aspect of the invention, the inclined curved surface has a radius of curvature of 15.8 mm or more.

The sixth aspect of the invention is characterized in that, in addition to the configuration according to the first to fifth aspects of the invention, the plunger rod includes a plate-like plate part, and a rod part continuous with the plate part and receiving a force from the plate part, the plate part being provided with a recess on one surface opposite from a surface continuous with the rod part.

Effects of the Invention

The present invention allows the sense of feel when in use with fingers rested on the finger grip to be improved.

BRIEF DESCRIPTION OF THE DRAWINGS

FIG. 11 is a diagram showing the results of votes with respect to the ease of use of syringes in a first sensory test.

FIG. 12 is a diagram showing which syringe ranked top in average score in each step of a second sensory test.

FIG. 13 is a diagram showing the breakdown of rating in the second sensory test.

EMBODIMENTS OF THE INVENTION

Figure 1:
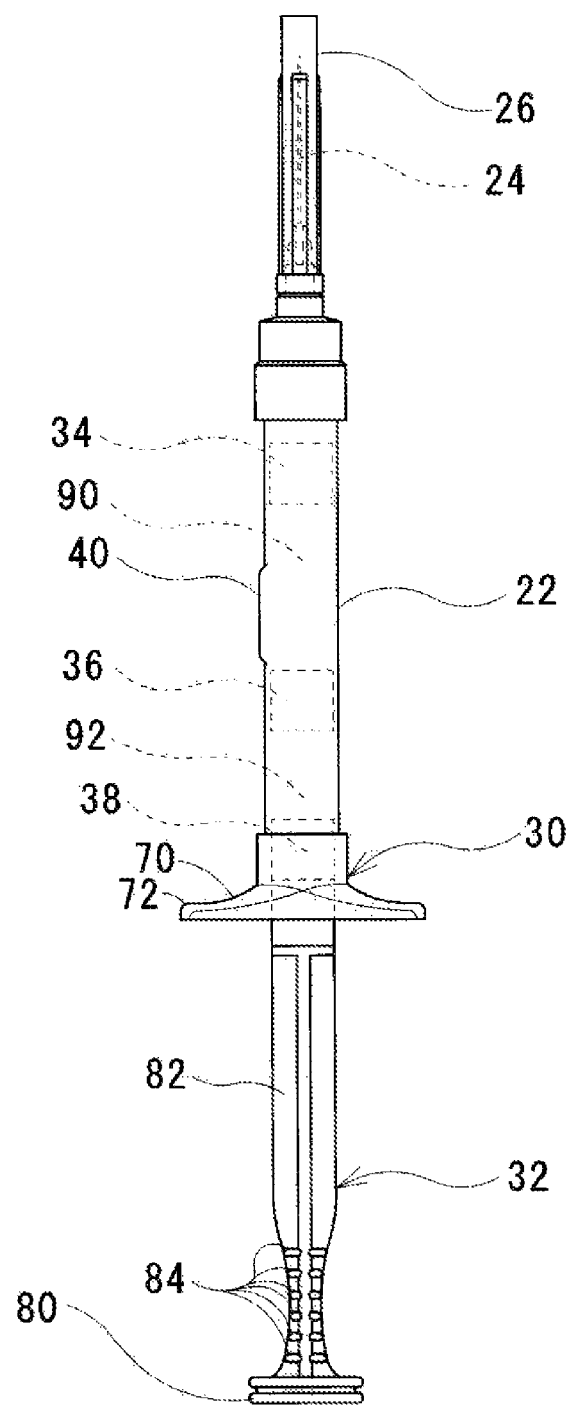
FIG. 1 is an external view of a syringe according to a first embodiment of the present invention.

Hereinafter the embodiments of the present invention will be described with reference to the drawings. In the description below, the same components are given the same reference numerals. These components have the same names and functions. Therefore, these components will not be repeatedly described in detail.

[Description of Syringe Configuration]

FIG. 1 is an external view of the syringe according to this embodiment. The syringe according to this embodiment includes a cylinder 22, a syringe needle 24, a syringe needle cover 26, a finger grip 30, a plunger rod 32, a front stopper 34, a middle stopper 36, and an end stopper 38. The cylinder 22 accommodates a first contained substance (not shown) such as a medical agent in powder form and a second contained substance (not shown) such as a liquid solution. A bypass 40 is formed midway in the cylinder 22. The syringe needle 24 is connected to one end of the cylinder 22. The first contained substance and second contained substance in the cylinder 22 are injected into the body of a patient through the syringe needle 24. The syringe needle cover 26 covers the syringe needle 24. The syringe needle cover 26 is removed when the first contained substance and second contained substance in the cylinder 22 are injected into the body of the patient. The finger grip 30 is connected to the other end of the cylinder 22. The finger grip 30 prevents the cylinder 22 from slipping off of the fingers of the syringe user (hereinafter referred to as "medical worker") as well as stabilizes the hand movement when the plunger rod 32 is pushed forward and when the first contained substance and second contained substance in the cylinder 22 are injected into the body of the patient. The plunger rod 32 is one that is commonly referred to as "syringe plunger rod". The plunger rod 32 extends through the finger grip 30 into the cylinder 22. The plunger rod 32 is attached such as to connect to the end stopper 38 so that when it is pushed forward, the plunger rod applies pressure to the second contained substance inside the cylinder 22. The front stopper 34, middle stopper 36, and end stopper 38 are accommodated in the cylinder 22. The front stopper 34 tightly seals the inside of the cylinder 22 from the outside. The middle stopper 36 partitions the inside of the cylinder 22 to a first chamber 90 and a second chamber 92. In this embodiment, the first contained substance is accommodated in the first chamber 90. The second contained substance is accommodated in the second chamber 92. The end stopper 38 tightly seals the inside of the cylinder 22 from the outside. The end stopper 38 receives the force from the plunger rod 32 and pushes the second contained substance (not shown) accommodated in the cylinder 22.

[Description of Finger Grip Configuration]

Figure 2:
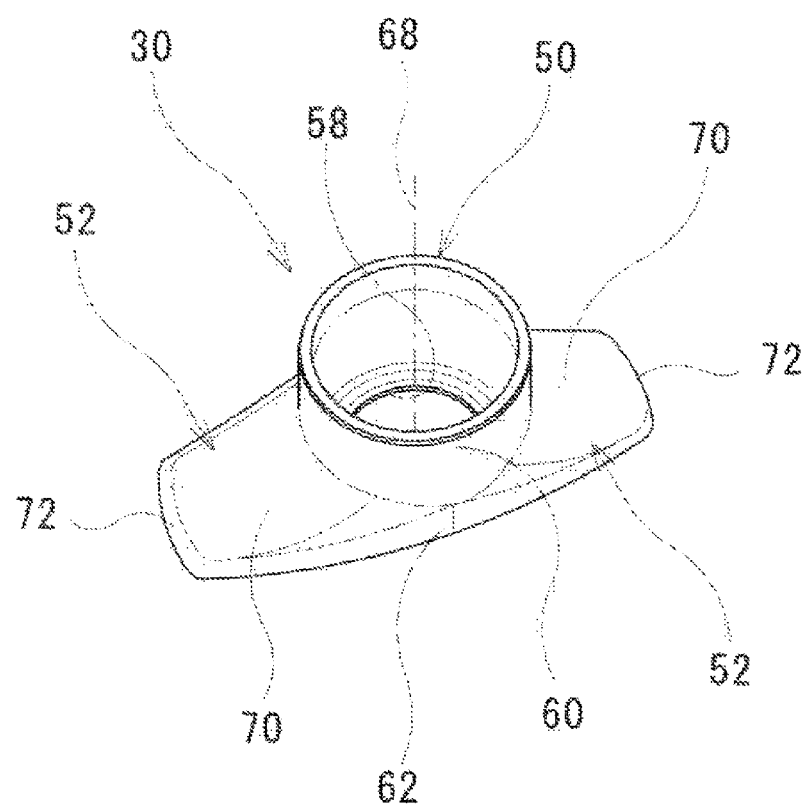
FIG. 2 is an external view of a finger grip according to the first embodiment of the present invention.
Figure 3:
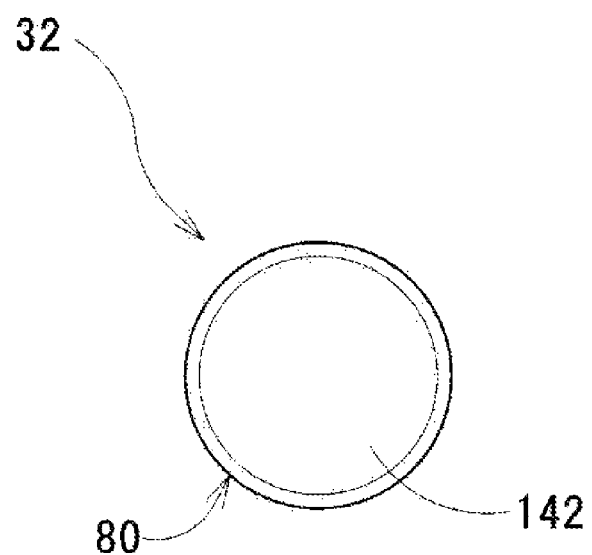
FIG. 3 is a front view of a plunger rod according to the first embodiment of the present invention.
Figure 4:
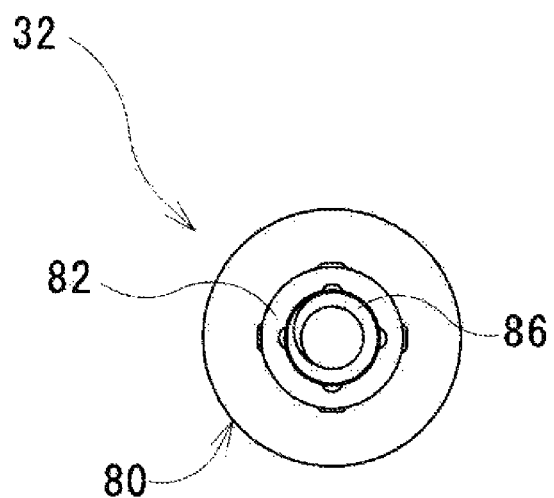
FIG. 4 is a rear view of the plunger rod according to the first embodiment of the present invention.

FIG. 2 is an external view of the finger grip 30 according to this embodiment. The finger grip 30 according to this embodiment will be described with reference to FIG. 2. The finger grip 30 according to this embodiment is made of polypropylene. The finger grip 30 according to this embodiment includes a cylindrical portion 50 and a pair of finger hook portions 52. In this embodiment, these portions are integral.

In this embodiment, the other end of the cylinder 22 is inserted to the cylindrical portion 50 from one end 60. The plunger rod 32 extends through from the other end 62 of the cylindrical portion 50. A circular protrusion 58 is provided on an inner circumferential surface of the cylindrical portion 50. The protrusion 58 catches the other end of the cylinder 22 so that the cylinder 22 is prevented from passing through and coming off of the cylindrical portion 50. The specific inner circumferential structure of the cylindrical portion 50 is similar to that of the cylindrical portion of the known finger grip. Therefore it will not be described here in detail.

The finger hook portions 52 are provided such as to protrude from an outer circumferential surface of the cylindrical portion 50. In this embodiment, the finger hook portions 52 are provided at the other end 62 of the outer circumferential surface of the cylindrical portion 50. The pair of finger hook portions 52 protrude to opposite directions. The finger hook portions 52 each have an inclined curved surface 70 and an end-side curved surface 72.

The inclined curved surface 70 is provided on one side surface of the finger hook portion 52 facing one end 60 of the cylindrical portion 50 (where the other end of the cylinder 22 is connected). In this embodiment, the inclined curved surface 70 extends from the proximal end to the distal end of the side surface of the finger hook portion 52. In this embodiment, as shown in FIG. 2, any area of the inclined curved surface 70 closer to the distal end of the side surface of the finger hook portion 52 is closer to the other end 62 of the cylindrical portion 50 than an area closer to the proximal end of the side surface of the inclined curved surface 70. Consequently, the closer to the distal end, the thinner the finger hook portion 52 becomes, as compared to an area closer to the proximal end. In this embodiment, the slope of an area on the proximal side of the inclined curved surface 70 relative to the center axis 68 of the cylindrical portion 50 is shallower than the slope of an area on the distal side relative to the center axis 68 of the cylindrical portion 50. Consequently, the farther from the cylindrical portion 50, the shallower the slope of the inclined curved surface 70 becomes relative to a plane direct to the center axis 68 of the cylindrical portion 50. It goes without saying that the inclined curved surface 70 can have a constant radius of curvature in a cross section parallel to the direction in which the finger hook portion 52 protrudes. In the following description, the radius of curvature simply associated with the inclined curved surface 70 shall mean the radius of curvature of the inclined curved surface 70 in a cross section parallel to the direction in which the finger hook portion 52 protrudes.

The end-side curved surface 72 is located at the boundary between the tip of the finger hook portion 52 and the inclined curved surface 70. The end-side curved surface 72 extends along this boundary. Thus the boundary portion between the tip of the finger hook portion 52 and the inclined curved surface 70 is a curved surface. In this embodiment, the edge of the end-side curved surface 72 extends as far as to the tip of the finger hook portion 52. Namely, the edge of the end-side curved surface 72 is the tip of the finger hook portion 52. It goes without saying that the end-side curved surface 72 can have a constant radius of curvature in a cross section parallel to the direction in which the finger hook portion 52 protrudes. In the following description, the radius of curvature simply associated with the end-side curved surface 72 shall mean the radius of curvature of the end-side curved surface 72 in a cross section parallel to the direction in which the finger hook portion 52 protrudes.

In this embodiment, the length obtained by subtracting twice the radius of curvature of the end-side curved surface 72 and the outside diameter of the cylindrical portion 50 from a maximum length between the tip of one finger hook portion 52 and the tip of the other finger hook portion 52 has a significant impact on the sense of feel when in use with fingers rested on the finger grip 30. When this value is 19.2 mm or more, the sense of feel when in use with fingers rested on the finger grip 30 is significantly improved as compared to when not. When this value is from 19.2 mm or more to 22.2 mm or less, the sense of feel when in use with fingers rested on the finger grip 30 is improved further as compared to when not. When this value is from 19.2 mm or more to 20 mm or less, the sense of feel when in use with fingers rested on the finger grip 30 is improved even more as compared to when not. When this value is from 19.2 mm or more to 20 mm or less, the radius of curvature of the inclined curved surface 70 has a significant impact on the sense of feel when in use with fingers rested on the finger grip 30. In this case, when the radius of curvature is 15.8 mm or more, the sense of feel when in use with fingers rested on the finger grip 30 is improved even more than when the radius of curvature is less than 15.8 mm.

Figure 5:
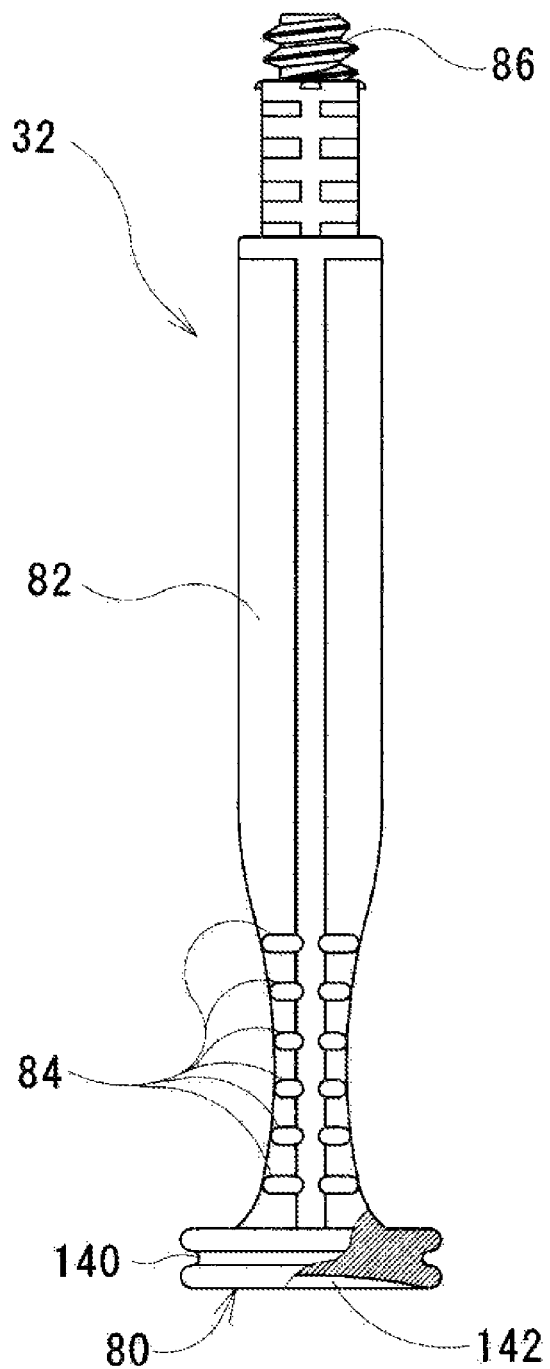
FIG. 5 is a plan view of the plunger rod according to the first embodiment of the present invention.
Figure 6:
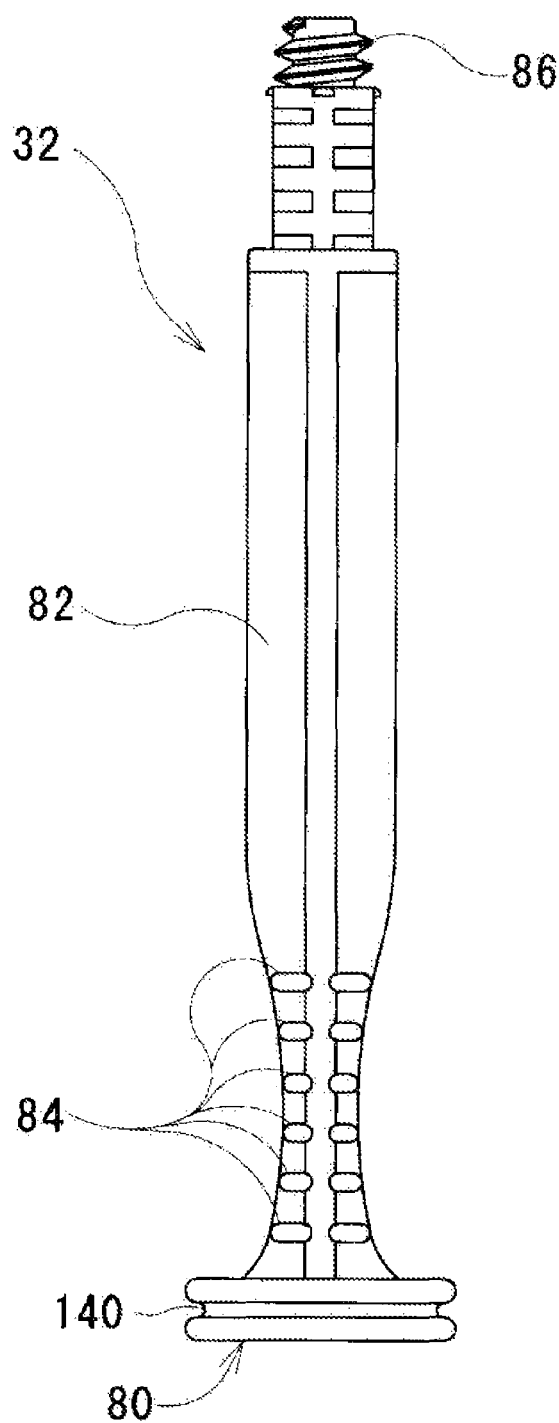
FIG. 6 is a bottom view of the plunger rod according to the first embodiment of the present invention.
Figure 7:
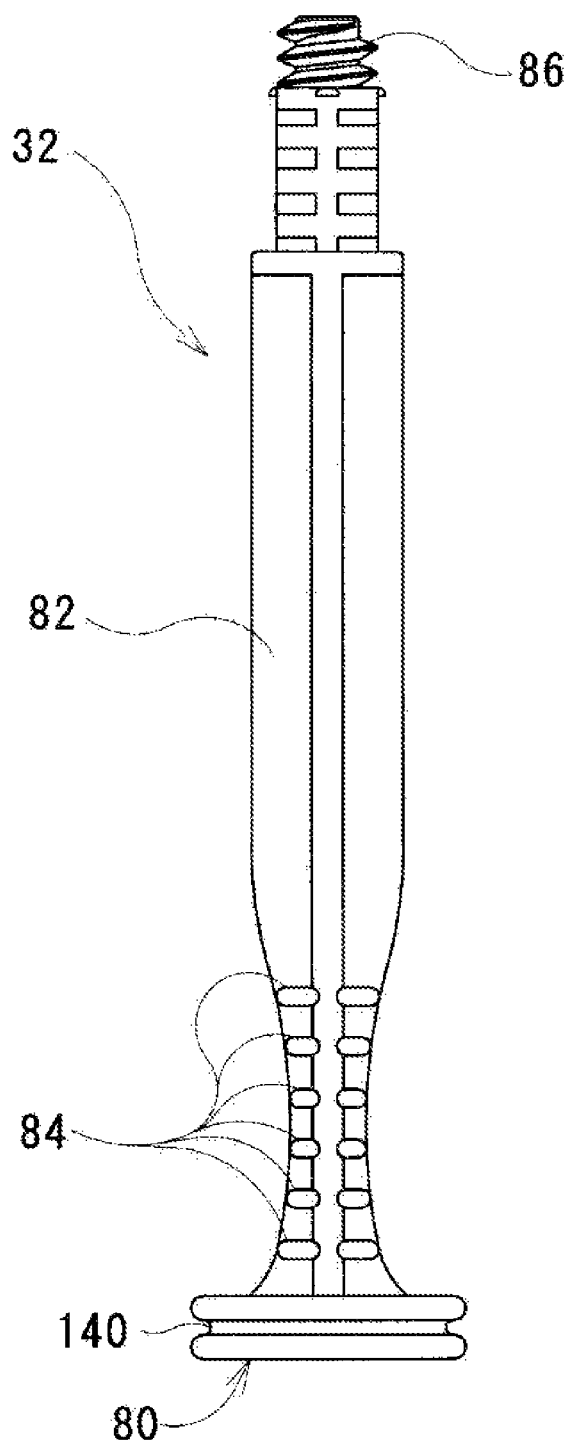
FIG. 7 is a right side view of the plunger rod according to the first embodiment of the present invention.
Figure 8:
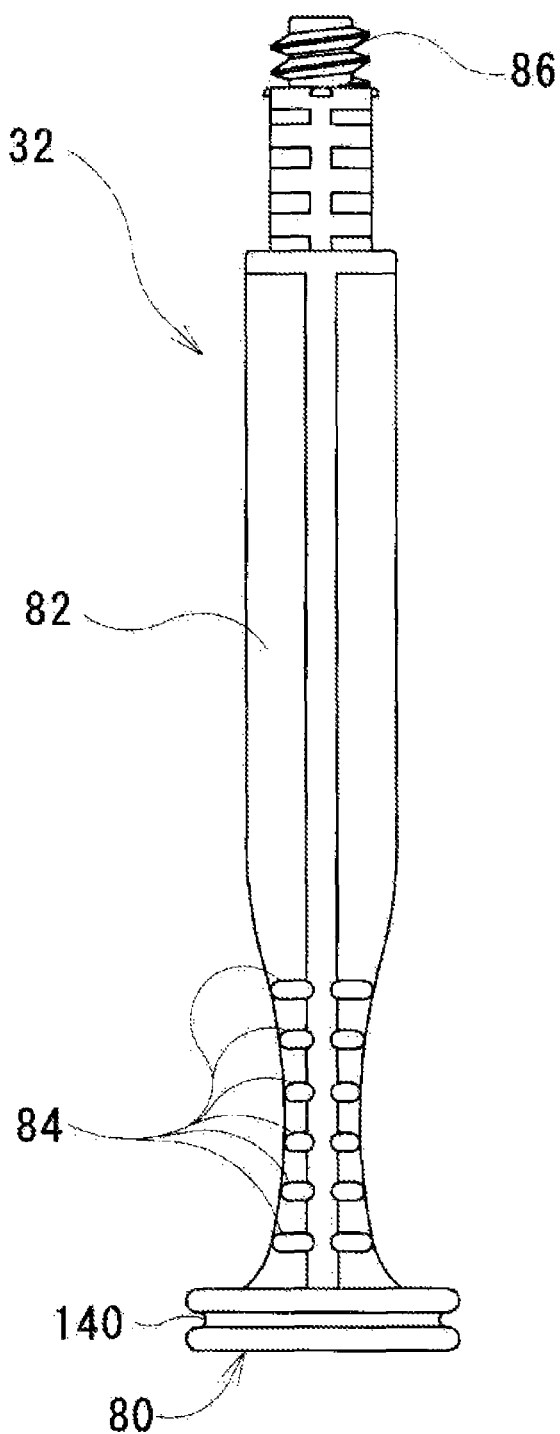
FIG. 8 is a left side view of the plunger rod according to the first embodiment of the present invention.

FIG. 3 to FIG. 8 are external views of the plunger rod 32 according to this embodiment. In FIG. 5, part of the plunger rod 32 is removed. The removed part has the same shape as part of the bottom view shown in FIG. 6 corresponding to the removed part in FIG. 5. The plunger rod 32 according to this embodiment will be described with reference to FIG. 3 to FIG. 8. The plunger rod 32 according to this embodiment includes a plate part 80, a rod part 82, ribs 84, and a stopper connector 86. A finger of a medical worker makes contact with the plate part 80. The plate part 80 receives a force from the medical worker's finger. The rod part 82 transmits the force received by the plate part 80 to the end stopper 38. The ribs 84 reinforce the rod part 82. The stopper connector 86 is connected to the end stopper 38.

In this embodiment, the plate part 80 is in a circular disc form. A groove 140 is formed in the outer circumference of the plate part 80. As clear from FIG. 3 and FIG. 5, a recess 142 is provided on the backside of the plate part 80 (the surface which the medical worker's finger will contact when the syringe according to this embodiment is used) opposite from the side adjacent the ribs 84 (side connecting to the rod part 82).

In this embodiment, the recess 142 provided in the plate part 80 is formed as a curved surface. The center of the curved surface (where it is deepest) has a depth of 1.0 mm from the edge. The edge of the plate part 80 is curved and continuous with the inner part of the plate. When the curved surface at the edge of the plate part 80 has a radius of curvature of 0.75 mm, if the plate part 80 is circular with a diameter of 17.5 mm, the recess 142 has a radius of curvature of 31.8 mm, and if the plate part 80 is circular with a diameter of 20 mm, the recess 142 has a radius of curvature of 42.9 mm.

In this embodiment, the rod part 82 is made up of four plate-like portions. These plate-like portions are disposed such that the rod part 82 has a cross section in the shape of a cross. The ribs 84 are provided to connect adjacent pairs of these plate-like portions. The stopper connector 86 is in the shape of a male thread. This is for connecting to a female thread (not shown) provided to the end stopper 38.

[Description of Method of Use]

The method of use of the syringe according to this embodiment is similar to that of known syringes. Namely, in preparation of drug administration, a medical worker presses the plunger rod 32, with the syringe needle 24 facing upwards. When the plunger rod 32 is pushed, the end stopper 38 moves towards the syringe needle 24. With this, the middle stopper 36 moves too. In this movement, the middle stopper 36 reaches a point where the bypass 40 is provided. By the middle stopper 36 reaching there, a state wherein the first chamber 90 and the second chamber 92 are first in fluid communication is achieved (hereinafter referred to as "fluid motion initiation state"). As the pressure in the first chamber 90 is raised by the movement of the middle stopper 36, the front stopper 34 also moves against the frictional force between itself and the inner surface of the cylinder 22.

When the medical worker further presses the plunger rod 32 forward (and in turn the end stopper 38) from the fluid motion initiation state, the second contained substance in the second chamber 92 moves into the first chamber 90 via the bypass 40. The pressure in the first chamber 90 rises as the second contained substance flows in, so that the front stopper 34 moves toward the syringe needle 24 against the frictional force between itself and the inner surface of the cylinder 22. Sometimes, when the second contained substance in the second chamber 92 has moved into the first chamber 90 via the bypass 40, the rod advancement is stopped, to cause the first contained substance in the first chamber 90 to mix with the second contained substance that has transferred therein.

After that, when the medical worker further presses the plunger rod 32 forward (and in turn the end stopper 38), the front stopper 34 reaches one end of the cylinder 22 where the syringe needle 24 is attached. The cylinder 22 is connected to a syringe needle fixing member 28 in this part. A stopper accommodating part (not shown) is formed inside the syringe needle fixing member 28. A communication groove in the form of a recess (not shown) is formed in the inner wall of the stopper accommodating part. The first chamber 90 communicates with the outside of the syringe via this groove. When the medical worker further presses the plunger rod 32 forward (and in turn the end stopper 38) in this state, the air inside the first chamber 90 is pushed out.

After that, the medical worker removes the syringe needle cover 26, and inserts the syringe needle 24 in the patient. When the syringe needle 24 is inserted in the patient, the medical worker pushes the plunger rod 32. Thus the first contained substance and the second contained substance are injected into the body of the patient through the syringe needle 24.

When the injection is a subcutaneous injection, after the syringe needle 24 has been inserted in the patient, a "blood backflow check" is usually performed before the plunger rod 32 is pushed, which is pulling back the plunger rod 32 slightly, to check if the needle has not entered a blood vessel.

[Description of the Effects of the Syringe According to this Embodiment]

In this embodiment, the finger hook portion 52 has an inclined curved surface 70 and an end-side curved surface 72. Anywhere on the inclined curved surface 70, the inclined curved surface 70 is closer to the other end 62 of the cylindrical portion 50 in an area corresponding to a distal side of the side surface of the finger hook portion 52 than in an area corresponding to a proximal side of the side surface. In this embodiment, the slope of an area on the proximal side of the inclined curved surface 70 relative to the center axis 68 of the cylindrical portion 50 is shallower than the slope of an area on the distal side relative to the center axis 68 of the cylindrical portion 50. This way, the shape of the inclined curved surface 70 is closer to the shape of the surface of a human finger as compared to when the side surface of the finger hook portion 52 facing one end 60 of the cylindrical portion 50 (where the other end of the cylinder 22 is connected) is flat. As the end-side curved surface 72 is disposed in the boundary between the tip of the finger hook portion 52 and the inclined curved surface 70 and extends along this boundary, the boundary portion between the tip of the finger hook portion 52 and the inclined curved surface 70 is curved. In this way, it is less likely that this boundary portion bites into the medical worker's finger, as compared to the case when the boundary portion between the tip of the finger hook portion 52 and the inclined curved surface 70 is angled. As a result, the sense of feel when in use with fingers rested on the finger grip 30 can be improved.

When the length obtained by subtracting twice the radius of curvature of the end-side curved surface 72 and the outside diameter of the cylindrical portion 50 from a length between the tip of one finger hook portion 52 and the tip of the other finger hook portion 52 is 19.2 mm or more, the sense of feel when in use with fingers rested on the finger grip 30 is significantly improved as compared to when it is not. When this value is from 19.2 mm or more to 22.2 mm or less, the sense of feel when in use with fingers rested on the finger grip 30 is improved further as compared to when not. When this value is from 19.2 mm or more to 20 mm or less, the sense of feel when in use with fingers rested on the finger grip 30 is improved even more as compared to when not. When this value is from 19.2 mm or more to 20 mm or less, the radius of curvature of the inclined curved surface 70 has a significant impact on the sense of feel when in use with fingers rested on the finger grip 30. When this radius of curvature is 15.8 mm or more, the sense of feel when in use with fingers rested on the finger grip 30 is improved even more than when the radius of curvature is less than 15.8 mm.

Also, when there is provided the recess 142 on the plate part 80 of the plunger rod 32 on the opposite side from the side adjacent to the ribs 84, the sense of feel when in use with a finger put there is improved as compared to when this side is flat.

DESCRIPTION OF OTHER EMBODIMENTS

The embodiment disclosed here is illustrative only in every aspect. The scope of the present invention should not be limited based on the embodiment described above, and it goes without saying that various design modifications may be made without departing from the subject matter of the present invention.

Figure 9:
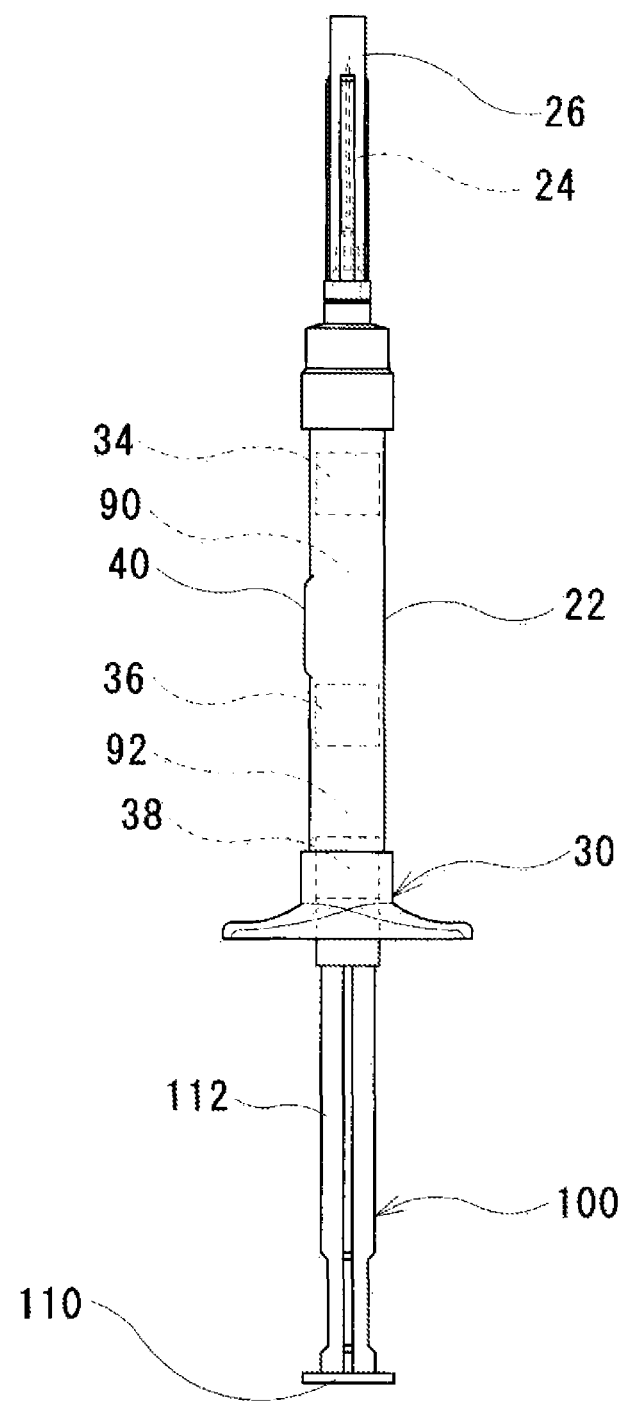
FIG. 9 is an external view of a syringe according to a second embodiment of the present invention.

For example, the shape of the plunger rod 32 is not limited to the one described above. FIG. 9 is an external view of a syringe according to a second embodiment of the present invention. The syringe according to this embodiment includes a plunger rod 100 instead of the plunger rod 32. The plunger rod 100 according to this embodiment includes a plate part 110, a rod part 112, and a stopper connector 86. A finger of a medical worker makes contact with the plate part 110. The plate part 110 receives a force from the finger. The rod part 112 transmits the force received by the plate part 110 to the end stopper 38.

In this embodiment, the plate part 110 is in a circular disc form. No groove is formed in the outer circumference of the plate part 110. In the plate part 110 of this embodiment, no recess is provided unlike the plate part 80 of the first embodiment. The surface of the plate part 110 opposite from the side where the rod part 112 protrudes (the surface which the medical worker's finger contacts when the syringe of this embodiment is used) is flat.

The structure of the cylinder 22 is not limited to the one described above. For example, the cylinder according to the present invention need not include the bypass 40. In this case, the cylinder according to the present invention need not include the middle stopper 36 and the front stopper 34. In this case, the cylinder according to the present invention may include the end stopper 38 and the front stopper 34 but need not include the middle stopper 36.

The material of the syringe according to the present invention is not limited particularly. The material of the syringe needle 24, however, in the syringe according to the present invention, should preferably be metal, and other parts should preferably be made of either synthetic resin or glass.

DESCRIPTION OF WORKING EXAMPLES

Working Example 1

A maker fabricated the finger grip 30 shown in FIG. 2 by an injection molding method. The material of the finger grip 30 was polypropylene. The cylindrical portion 50 had an outside diameter d of 15 mm. The inside diameter was 12.3 mm. The length of the cylindrical portion 50 (from one end to the other end) was 14 mm. The protrusion 58 on the inner circumferential surface of the cylindrical portion 50 had an inside diameter of 9.7 mm.

The entire width of the finger hook portions (from the end of one finger hook portion 52 to the end of the other finger hook portion) W of the finger grip 30 was 38 mm. The radius of curvature $R_1$ of the inclined curved surface 70 was 15.8 mm. The radius of curvature $R_2$ of the end-side curved surface 72 was 1.5 mm. The length obtained by subtracting twice the radius of curvature $R_2$ of the end-side curved surface 72 and the outside diameter d of the cylindrical portion 50 from the entire width W of the finger hook portions (which substantially equals to the length from the edge at the distal end of one end-side curved surface 72 to the edge at distal end of the other end-side curved surface 72) was 20 mm.

Next, the maker fabricated the plunger rod 32 shown in FIG. 3 to FIG. 8 by an injection molding method. The material of the plunger rod 32 was polypropylene. The size of the stopper connector 86 of the plunger rod 32 was set in accordance with the female thread (not shown) of the end stopper 38. The size of the rod part 82 was set slightly smaller than the inside diameter of the cylinder 22. The center of the recess 142 of the plate part 80 (where it is deepest) had a depth of 1 mm from the edge.

Next, the maker passed the plunger rod 32 through the finger grip 30. Next, the maker connected the plunger rod 32 to the end stopper 38. Next, the maker accommodated the front stopper 34, middle stopper 36, and the end stopper 38 to which the plunger rod 32 is connected, in the cylinder 22. In doing so, the maker encased the first contained substance and the second contained substance, too. Next, the maker connected the finger grip 30 with the plunger rod 32 passing therethrough to the cylinder 22. Next, the maker connected the syringe needle 24 to the cylinder 22. Lastly, the maker put the syringe needle cover 26 on the syringe needle 24. The cylinder 22, syringe needle 24, syringe needle cover 26, front stopper 34, middle stopper 36, and end stopper 38 were those of Leuplin (Registered Trademark) produced by Takeda Pharmaceutical Company Ltd. Therefore the specific shapes and production methods of those will not be described in detail. The syringe according to this working example was thus completed.

Working Example 2

The finger hook portions of this finger grip 30 according to this working example had an entire width W of 35 mm. The radius of curvature $R_1$ of the inclined curved surface 70 was 10 mm. The radius of curvature $R_2$ of the end-side curved surface 72 was 0.4 mm. The value obtained by subtracting twice the radius of curvature $R_2$ of the end-side curved surface 72 and the outside diameter d of the cylindrical portion 50 from the entire width W of the finger hook portions was 19.2 mm. Other features of the finger grip 30 according to this working example are similar to Working Example 1. In particular, the cylinder 22, syringe needle 24, syringe needle cover 26, plunger rod 32, front stopper 34, middle stopper 36, and end stopper 38 had exactly the same shapes as those of Working Example 1.

Working Example 3

The finger hook portions of this finger grip 30 according to this working example had an entire width W of 38 mm. The radius of curvature $R_1$ of the inclined curved surface 70 was 15.8 mm. The radius of curvature $R_2$ of the end-side curved surface 72 was 0.4 mm. The value obtained by subtracting twice the radius of curvature $R_2$ of the end-side curved surface 72 and the outside diameter d of the cylindrical portion 50 from the entire width W of the finger hook portions was 22.2 mm. Other features of the finger grip 30 according to this working example are similar to Working Example 1. In particular, the cylinder 22, syringe needle 24, syringe needle cover 26, plunger rod 32, front stopper 34, middle stopper 36, and end stopper 38 had exactly the same shapes as those of Working Example 1.

Working Example 4

The finger hook portions of this finger grip 30 according to this working example had an entire width W of 38 mm. The radius of curvature $R_1$ of the inclined curved surface 70 was 10 mm. The radius of curvature $R_2$ of the end-side curved surface 72 was 0.4 mm. The value obtained by subtracting twice the radius of curvature $R_2$ of the end-side curved surface 72 and the outside diameter d of the cylindrical portion 50 from the entire width W of the finger hook portions was 22.2 mm. Other features of the finger grip 30 according to this working example are similar to those of Working Example 1. In particular, the cylinder 22, syringe needle 24, syringe needle cover 26, plunger rod 32, front stopper 34, middle stopper 36, and end stopper 38 had exactly the same shapes as those of Working Example 1.

Working Example 5

The finger hook portions of this finger grip 30 according to this working example had an entire width W of 35 mm. The radius of curvature $R_1$ of the inclined curved surface 70 was 12.5 mm. The radius of curvature $R_2$ of the end-side curved surface 72 was 0.4 mm. The value obtained by subtracting twice the radius of curvature $R_2$ of the end-side curved surface 72 and the outside diameter d of the cylindrical portion 50 from the entire width W of the finger hook portions was 19.2 mm. Other features of the finger grip 30 according to this working example are similar to Working Example 1. In particular, the cylinder 22, syringe needle 24, syringe needle cover 26, plunger rod 32, front stopper 34, middle stopper 36, and end stopper 38 had exactly the same shapes as those of Working Example 1.

Working Example 6

The finger hook portions of this finger grip 30 according to this working example had an entire width W of 35 mm. The radius of curvature $R_1$ of the inclined curved surface 70 was 12.5 mm. The radius of curvature $R_2$ of the end-side curved surface 72 was 1.5 mm. The value obtained by subtracting twice the radius of curvature $R_2$ of the end-side curved surface 72 and the outside diameter d of the cylindrical portion 50 from the entire width W of the finger hook portions was 17 mm. Other features of the finger grip 30 according to this working example are similar to those of Working Example 1. In particular, the cylinder 22, syringe needle 24, syringe needle cover 26, plunger rod 32, front stopper 34, middle stopper 36, and end stopper 38 had exactly the same shapes as those of Working Example 1.

Comparative Example 1

Figure 10:
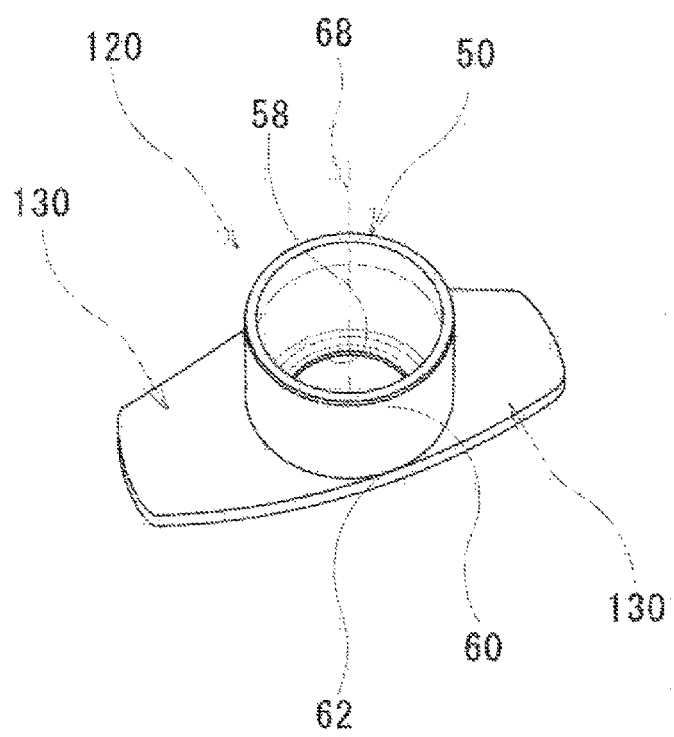
FIG. 10 is an external view of a finger grip according to a comparative example.

FIG. 10 is an external view of a finger grip 120 according to a comparative example. The finger grip 120 of the comparative example was made of polypropylene as with the finger grip 30 according to Working Example 1. The finger grip 120 according to this comparative example includes a cylindrical portion 50 and a pair of finger hook portions 130. In this comparative example, these portions are integral. The finger hook portions 130 are provided such as to protrude from an outer circumferential surface of the cylindrical portion 50. In this comparative example, the finger hook portions 130 are provided at the other end 62 of the outer circumferential surface of the cylindrical portion 50. The pair of finger hook portions 130 protrude to opposite directions. The finger hook portions 130 have a flat plate shape. The shape and size of this finger grip 120 are the same as those of Leuplin (Registered Trademark) produced by Takeda Pharmaceutical Company Ltd. Other features of the finger grip 120 of the comparative example are similar to those of the finger grip 30 according to Working Example 1.

After fabricating the finger grip 120, the maker assembled the syringe in the steps similar to Working Example 1. The cylinder 22, syringe needle 24, syringe needle cover 26, plunger rod 32, front stopper 34, middle stopper 36, and end stopper 38 used in the assembling had exactly the same shapes as those of Working Example 1.

Comparative Example 2

The syringe according to this comparative example was that of Leuplin (Registered Trademark) produced by Takeda Pharmaceutical Company Ltd. The shape and size of the plunger rod of this syringe were the same as those of the plunger rod 100 shown in FIG. 9. As mentioned above, the finger grip of this syringe has the same shape as that of Comparative Example 1. Other features of the syringe according to this comparative example are the same as those of the syringes according to Working Examples 1 to 6.

[Description of First Sensory Test]

Nine each syringes were made according to Working Examples 1 to 6. Nine medical workers compared the ease of use of the syringes according to Working Examples 1 to 6 in terms of the following aspects. The first aspect was the ease of holding the syringe. The second aspect was the ease of transfer of the second contained substance from the second chamber 92 to the first chamber 90 before the air was pushed out (operation of pushing the plunger rod 32 with the syringe needle 24 facing upward so as to push out the air inside the cylinder 22). The third aspect was the ease of discharging the first contained substance and second contained substance inside the cylinder 22. The nine medical workers selected the most easy-to-use syringe and the next most easy-to-use syringe in these criteria. Multiple choice was allowed in selecting the syringes. Namely, multiple syringes could be selected as the "most easy-to-use syringe". Similarly, multiple syringes could be selected as the "next most easy-to-use syringe". FIG. 11 is a diagram showing the results of votes with respect to the ease of use of the syringes according to Working Examples 1 to 6. The results of votes were calculated as follows. First, for each of Working Examples 1 to 6, the sum of the number of medical workers who chose Working Example 1 (or 2, 3, . . . 6) as the "most easy-to-use syringe", and the number of medical workers who chose Working Example 1 (or 2, 3, . . . 6) as the "next most easy-to-use syringe" was calculated. Once calculated, these sums were divided by the number of aspects (in this case, the ease of use of the syringes was compared based on three aspects. Therefore the "number of aspects" is "3"). The values calculated this way are shown in the section "first and second" in the "number of votes" in FIG. 11. Also, for each of Working Examples 1 to 6, the number of medical workers who chose Working Example 1 (or 2, 3, . . . 6) as the "most easy-to-use syringe" was divided by the number of aspects. The values calculated this way are shown in the section "first only" in the "number of votes" in FIG. 11. One can see from FIG. 11 that the syringe having the finger grip 30 according to Working Example 1 and the syringe having the finger grip 30 according to Working Example 2 received high ratings. The syringe having the finger grip 30 according to Working Example 3 and the syringe having the finger grip 30 according to Working Example 4 obtained the next highest ratings. The syringe having the finger grip 30 according to Working Example 5 came next in rank. The syringe having the finger grip 30 according to Working Example 6 came next in rank. This indicates that the value obtained by subtracting twice the radius of curvature $R_2$ of the end-side curved surface 72 and the outside diameter d of the cylindrical portion 50 from the entire width W of the finger hook portions should preferably be 19.2 mm or more. It indicates that it is more preferable if the value obtained by subtracting twice the radius of curvature $R_2$ of the end-side curved surface 72 and the outside diameter d of the cylindrical portion 50 from the entire width W of the finger hook portions is from 19.2 mm or more to 22.2 mm or less. It indicates that it is even more preferable if the value obtained by subtracting twice the radius of curvature $R_2$ of the end-side curved surface 72 and the outside diameter d of the cylindrical portion 50 from the entire width W of the finger hook portions is from 19.2 mm or more to 20 mm or less. It indicates that it is further preferable if the value obtained by subtracting twice the radius of curvature $R_2$ of the end-side curved surface 72 and the outside diameter d of the cylindrical portion 50 from the entire width W of the finger hook portions is from 19.2 mm or more to 20 mm or less, and the radius of curvature $R_1$ of the inclined curved surface 70 is 15.8 mm or more.

[Description of Second Sensory Test]

Thirty-two each syringes according to Working Example 1, Working Example 2, and Comparative Example 1 were made. Thirty-two syringes according to Comparative Example 2 were procured.

One each syringe according to Working Example 1, Working Example 2, Comparative Example 1, and Comparative Example 2 were handed to each of thirty-two medical workers. These medical workers performed an operation consisting of the following 6 steps to each of the syringes. The first step was a step of pushing the plunger rod 32 or 100 to move the second contained substance from the second chamber 92 to the first chamber 90. The second step was a step of flicking the cylinder 22 with the left hand while holding the syringe with the right hand on the finger grip 30 and the plunger rod 32 or 100 to cause the first contained substance in the first chamber 90 to be suspended in the second contained substance. The third step was a step of pushing the plunger rod 32 or 100 to push the air in the first chamber 90 out of the first chamber 90. The fourth step was a step of inserting the syringe needle 24 into a cushion used as a patient's body. The fifth step was a step of pulling back the plunger rod 32 or 100 slightly (simulating a blood backflow check). The sixth step was a step of pushing the plunger rod 32 or 100 (simulating subcutaneous administration of medication into the patient's body). The thirty-two medical workers evaluated the syringes according to Working Example 1, Working Example 2, and Comparative Example 1 whether they were easier to use as compared to the syringe according to Comparative Example 2 with respect to each of the steps. The syringe being evaluated was given one point for being better than the syringe according to Comparative Example 2. The syringe being evaluated was deducted one point for being worse than the syringe according to Comparative Example 2. The syringe being evaluated was given no point for being similar to the syringe according to Comparative Example 2 in terms of the ease of use. After the evaluation, the proportions of the thirty-two medical workers who gave one point, no point, and deducted one point were calculated for each of the steps. Once these proportions were obtained, the difference between the proportion of workers who gave one point and the proportion of workers who deducted one point was calculated for each of the steps. This is the average values of the scores in the second sensory test. Also, the sum of the square of the proportion of workers who gave one point and the square of the proportion of workers who deducted one point was calculated for each of the steps. This is the standard deviations of the scores in the second sensory test. Once the average values of the scores and the standard deviations of the scores were obtained, the syringe with the top average value of the scores was selected for each step. FIG. 12 is a diagram showing which syringe ranked top in average score in each step of the second sensory test. FIG. 13 is a diagram showing the breakdown of the rating in the second sensory test.

As shown in FIG. 12, the syringe according to Working Example 1 was rated highest for most of the steps. The syringe according to Comparative Example 1 was rated highest only for the third step. FIG. 13 shows, however, that there is hardly any difference in the rating between the syringe according to Working Example 1 and the syringe according to Comparative Example 1. FIG. 13 also shows that the syringe according to Working Example 1 was rated higher in respect of the ease of use for most of the steps as compared to the syringe according to Working Example 2. This also indicates that it is more preferable in terms of the ease of use particularly when the value obtained by subtracting twice the radius of curvature $R_2$ of the end-side curved surface 72 and the outside diameter d of the cylindrical portion 50 from the entire width W of the finger hook portions is from 19.2 mm or more to 20 mm or less, and the radius of curvature $R_1$ of the inclined curved surface 70 is 15.8 mm or more, compared to the any other cases.

DESCRIPTION OF REFERENCE SIGNS

22: Cylinder
24: Syringe needle
26: Syringe needle cover
30, 120: Finger grip
32, 100: Plunger rod
34: Front stopper
36: Middle stopper
38: End stopper
40: Bypass
50: Cylindrical portion
52, 130: Finger hook portion
58: Protrusion
60: One end
62: Other end
68: Center axis
70: Inclined curved surface
72: End-side curved surface
80, 110: Plate part
82, 112: Rod part
84: Rib
86: Stopper connector
90: First chamber
92: Second chamber
140: Groove
142: Recess

The invention claimed is:

1. A syringe comprising:
a cylinder;
a syringe needle connected to one end of the cylinder;
a finger grip connected to the other end of the cylinder; and
a plunger rod passing through the finger grip and entering into the cylinder,
the finger grip including
a cylindrical portion having one end and the other end, the cylinder being inserted from the one end, and the plunger rod extending through from the other end of the cylindrical portion, and
a pair of finger hook portions protruding from an outer circumferential surface of the cylindrical portion to opposite directions,
the pair of finger hook portions each including
an inclined curved surface located on one side surface of each finger hook portion facing the one end of the cylindrical portion and having an area on a proximal side of the one side surface and an area on a distal side of the one side surface, the area on the distal side of the one side surface being closer to the other end of the cylindrical portion than the area on the proximal side of the one side surface, and the area on the proximal side having a shallower slope with respect to a center axis of the cylindrical portion than the area on the distal side, and
an end-side curved surface disposed in a boundary between a tip of finger hook portion and the inclined curved surface and extending along the boundary, wherein the end-side curved surface extends as far as to the tip of each finger hook portion, and
a length obtained by subtracting twice a radius of curvature of the end-side curved surface and an outer diameter of the cylindrical portion from a length between the tip of one finger hook portion and the tip of the other finger hook portion is 19.2 mm or more.

2. The syringe according to claim 1, wherein the length obtained by subtracting twice the radius of curvature of the end-side curved surface and the outside diameter of the cylindrical portion from the length between the tip of one finger hook portion and the tip of the other finger hook portion is 22.2 mm or less.

3. The syringe according to claim 1, wherein the length obtained by subtracting twice the radius of curvature of the end-side curved surface and the outside diameter of the cylindrical portion from the length between the tip of one finger hook portion and the tip of the other finger hook portion is 20 mm or less.

4. The syringe according to claim 3, wherein the inclined curved surface has a radius of curvature of 15.8 mm or more.

5. The syringe according to claim 1, wherein
the plunger rod includes
a plate part, and
a rod part continuous with the plate part and receiving a force from the plate part,
the plate part being provided with a recess on one surface opposite from a surface continuous with the rod part.

* * * * *

UNITED STATES PATENT AND TRADEMARK OFFICE
CERTIFICATE OF CORRECTION

PATENT NO. : 11,219,718 B2
APPLICATION NO. : 16/497492
DATED : January 11, 2022
INVENTOR(S) : Atsushi Kanazawa et al.

It is certified that error appears in the above-identified patent and that said Letters Patent is hereby corrected as shown below:

In the Claims

Claim 1, Column 14, Line 34, please delete the phrase "between a tip of finger hook portion" and replace with "between a tip of each finger hook portion".

Signed and Sealed this
First Day of March, 2022

Drew Hirshfeld
*Performing the Functions and Duties of the*
*Under Secretary of Commerce for Intellectual Property and*
*Director of the United States Patent and Trademark Office*